United States Patent
Tanaka et al.

(10) Patent No.: US 6,576,761 B1
(45) Date of Patent: Jun. 10, 2003

(54) PROCESS FOR THE PREPARATION OF CEPHEM COMPOUNDS

(75) Inventors: Hideo Tanaka, Okayama (JP); Yutaka Kameyama, Tokushima (JP)

(73) Assignee: Otsuka Kagaku Kabushiki Kaisha, Osaka (JP)

( * ) Notice: Subject to any disclaimer, the term of this patent is extended or adjusted under 35 U.S.C. 154(b) by 0 days.

(21) Appl. No.: 10/049,048

(22) PCT Filed: Aug. 30, 2000

(86) PCT No.: PCT/JP00/05851

§ 371 (c)(1),
(2), (4) Date: Feb. 7, 2002

(87) PCT Pub. No.: WO01/16140

PCT Pub. Date: Mar. 8, 2001

(30) Foreign Application Priority Data

Sep. 1, 1999 (JP) .......................................... 11-247272

(51) Int. Cl.$^7$ ..................... C07D 501/22; C07D 501/24; C07D 501/16
(52) U.S. Cl. ...................... 540/215; 540/222; 540/227
(58) Field of Search ................................ 540/215, 222, 540/227

(56) References Cited

U.S. PATENT DOCUMENTS 4,246,405 A   1/1981   Takaya et al. ................. 544/16

FOREIGN PATENT DOCUMENTS

| EP | 431794 | 6/1991 |
| GB | 1391437 | 4/1975 |
| JP | 54-3087 | 1/1979 |

OTHER PUBLICATIONS

Tanaka, H.; Zhao, J.; Kumase, H.; J. Org. Chem. 2001; 66(2); 570–577.*
Database Crossfire Beilstein, Citation No. 5505458 and Reaction ID 2056854 *abstract* for Lel, Tetrahedron 46(3), 1990, 921.
Patent Abstracts of Japan, vol. 013, No. 549, Dec. 7, 1989 for JP 01 224331 A, Kanto Denka Kogyo Co., Ltd., Sep. 7, 1989 *abstract*.

Hideo Tanaka et al., "Reductive Cross–Coupling of 3–Substituted $\Delta^3$–Cephems with Alkenyl Halides in an Al/PbBr$_2$NiBr$_2$(bpy) Triplemental Redox System. Synthesis of 3–Alkenyl–$\Delta^3$–cephems", J. Org. Chem., vol. 66, pp. 570–577, 2001.

* cited by examiner

Primary Examiner—Mark L. Berch
(74) Attorney, Agent, or Firm—Wenderoth, Lind & Ponack, L.L.P.

(57) ABSTRACT

1. A process for preparing a 3-alkenylcephem compound or 3-norcephem compound of the formula (3) characterized in that an alkenyl halide of the formula (2), a nickel catalyst, a metal up to −0.3 (V/SCE) in standard oxidation reduction potential and a compound of a metal having a higher standard oxidation reduction potential than the metal are caused to act on a 3-cephem compound of the formula (1) in a solvent

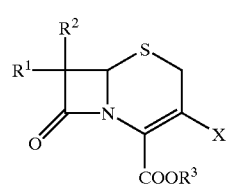

(1)

wherein $R^1$ is a hydrogen atom or the like, $R^2$ is a hydrogen atom or the like, $R^3$ is a hydrogen atom or carboxylic acid protective group, and X is a halogen atom or the like, $$R^4—Y \quad (2)$$

wherein $R^4$ is 1-alkenyl having or not having a substituent, and Y is a halogen atom

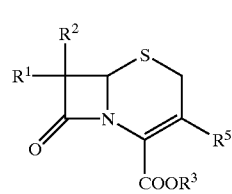

(3)

wherein $R^1$, $R^2$ and $R^3$ are as defined above, and $R^5$ is a hydrogen atom or 1-alkenyl having or not having a substituent.

4 Claims, No Drawings

PROCESS FOR THE PREPARATION OF CEPHEM COMPOUNDS

This application is the National Stage Application of PCT/JP00/05851 filed Aug. 30, 2000.

TECHNICAL FIELD

The present invention relates to a process for preparing a 3-alkenylcephem compound or 3-norcephem compound of the formula (3).

The 3-alkenylcephem compound or 3-norcephem compound of the formula (3) has the basic skeleton of a nonnatural antibiotic substance and is an important intermediate for preparing useful antimicrobial drugs having a wide antibacterial spectrum, such as cefixime and ceftibuten which are oral antibiotics generally in wide use (Katsuharu Sakai, "Handbook of Recent Antibiotics," 9th ed., pp. 83 and 85, 1994).

BACKGROUND ART

Already known as processes for preparing 3-alkenylcephem compounds are a process for subjecting a 3-halogenated methylcephem compound to Wittig reaction (e.g., JP-A-263990/1986), a process for introducing vinyl into a 3-sulfonyloxycephem compound utilizing a metallic catalyst [Tetrahedron Letters, 29, 6043 (1988), 31, 3389 (1990), 32, 4073 (1991), Journal of Organic Chemistry, 55, 5833 (1990)], a process wherein an allenyl β-lactam compound or halogenated β-lactam compound is used as the starting material [Tetrahedron Letters, 33, 7029 (1992), Journal of Organic Chemistry, 59, 4956 (1994), Synlett, 774 (1999)], etc.

However, the Wittig reaction mentioned first inevitably requires the treatment of a very large quantity of phosphorus by-product to be discarded since the reaction mechanism invariably forms a trialkyl or triaryl phosphine oxide in an amount equimolar to the starting material. The process for introducing vinyl into a 3-sulfonyloxycephem compound utilizing a metallic catalyst has a great industrial disadvantage in that the process not only requires the use of an expensive reagent which is sensitive to water in preparing the starting material but also requires an alkenyl tin compound or vinyl cuprate compound which must be used but is harmful to the reagent for alkenylation.

The process wherein an allenyl β-lactam compound is used as the starting material is difficult to practice industrially because the allenyl β-lactam compound serving as the starting compound is unstable and further because a combination of copper chloride and vinyltributyl tin or vinyl cuprate prepared from vinyltributyl tin is used as the reaction reagent.

The process wherein a halogenated β-lactam compound is used as the starting material has the problem of necessitating a multistep reaction procedure for preparing the starting material, requires the use of an organotin compound as an alkenylation reagent for the reaction, and still remains to be improved for realization.

Although these conventional techniques have found application to the preparation not only of 3-vinylcephem compounds but also of 3-alkenylcephem compounds, substantial problems have yet to be overcome.

On the other hand, reports have already been made on a process for preparing 3-norcephem compounds wherein zinc is caused to act, for example, on a 3-halocephem compound or 3-sulfonyloxycephem compound as the starting compound ([JP-A-59186/1977 and Recent Advances in the Chemistry of β-Lactam Antibiotics, 170(1977), and Pure & Appl. Chem., 59, 1041(1987)]. However, this process requires the use of a large amount of acetic acid, formic acid or trifluoroacetic acid and is difficult to practice.

Reports are also made on a process comprising catalytically hydrogenating first a 3-hydroxycephem compound serving as the starting material to obtain a 3-hydroxycepham compound and thereafter subjecting the compound to 1,2-elimination reaction with use of a haloformic acid ester/base to obtain a 3-norcephem compound (JP-A-213785/1983 and JP-A-34714/1983, or Pure & Appl. Chem., 59, 1041 (1987)]. This process requires the two steps of catalytic hydrogenation and 1,2-elimination reaction for the preparation of the desired compound and can not be a practically useful process.

A report is also made on a process wherein 3-formylcephem is used as the starting material, and a process wherein the Wittig reaction is used (Chemistry and Biology of β-Lactam Antibiotics, Penicillins and Cephalosporins, Vol. 1, 170), whereas the starting materials for both of these processes are compounds which are very difficult to obtain, the former requires the use of an expensive rhodium complex, and the latter has the problem that the Wittig reaction utilized forms a large amount of phosphorus by-product which must be disposed of.

An object of the present invention is to provide an industrially feasible process for preparing a 3-alkenylcephem compound or 3-norcephem compound from a 3-cephem compound of the formula (1) and serving as the starting material.

Stated more specifically, in a process for preparing with ease a 3-alkenylcephem compound or 3-norcephem compound by causing an alkenyl halide of the formula (2), a nickel catalyst, a metal up to −0.3 (V/SCE) in standard oxidation reduction potential and a compound of a metal having a higher standard oxidation reduction potential than the metal to act on a 3-cephem compound, the invention provides a novel technique capable of selectively producing one of the 3-alkenylcephem compound and the 3-norcephem compound merely by changing the solvent to be used in the process.

DISCLOSURE OF THE INVENTION

The present invention provides a process for selectively preparing a 3-alkenylcephem compound or 3-norcephem compound from a 3-cephem compound of the formula (1) and serving as the starting material.

The invention provides a process for preparing a 3-alkenylcephem compound or 3-norcephem compound of the formula (3) characterized in that an alkenyl halide of the formula (2), a nickel catalyst, a metal up to −0.3 (V/SCE) in standard oxidation reduction potential and a compound of a metal having a higher standard oxidation reduction potential than the metal are caused to act on a 3-cephem compound of the formula (1) in a solvent

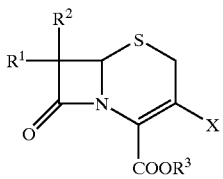

(1)

wherein $R^1$ is a hydrogen atom, halogen atom, amino or protected amino, $R^2$ is a hydrogen atom, halogen atom, lower alkoxyl, lower acyl, hydroxyl, protected hydroxyl, or lower alkyl having or not having hydroxyl or protected hydroxyl as a substituent, $R^3$ is a hydrogen atom or carboxylic acid protective group, and X is a halogen atom, lower alkylsulfonyloxy having or not having a substituent or an arylsulfonyloxy having or not having a substituent $$R^4—Y \quad (2)$$

wherein $R^4$ is 1-alkenyl having or not having a substituent, and Y is a halogen atom

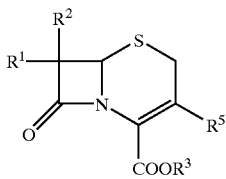

(3)

wherein $R^1$, $R^2$ and $R^3$ are as defined above, and $R^5$ is a hydrogen atom or 1-alkenyl having or not having a substituent.

According to the present invention, a 3-alkenylcephem compound can be prepared selectively with a high purity in a high yield by causing an alkenylation reagent, which are relatively safe to the human body and have high universal usefulness, to act on a 3-cephem compound having high stability, readily available and represented by the formula (1). Furthermore, a 3-norcephem compound can be selectively prepared with a high purity and in a high yield by changing the reaction condition. Thus one of the two kinds of nonnatural cephem skeletons can be readily prepared selectively.

Examples of groups referred to in the present invention are as follows. Unless otherwise specified, the term "halogen atom" as used herein refers to fluorine, chlorine, bromine or iodine, and the term "lower alkyl" means a straight-chain or branched alkyl group having 1 to 4 carbon atoms, such as methyl, ethyl, n-propyl, isopropyl, n-butyl, isobutyl, sec-butyl or tert-butyl.

The term "aryl" means, for example, phenyl, naphthyl or the like.

Exemplary of the protected amino represented by $R^1$ are amido groups such as phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, thienylacetamido, phenylacetoxyacetamido, α-oxophenylacetamido, benzamido, p-methylbenzamido, p-methoxybenzamido, p-chlorobenzamido, p-bromobenzamido, phenylglycylamido, phenylglycylamido having protected amino, p-hydroxyphenylglycylamido, p-hydroxyphenylglycylamido having protected amino and/or protected hydroxyl, etc.; imido groups such as phthalimido, nitrophthalimido, etc., in addition to the groups disclosed in Theodora W. Greene, 1981, "Protective Groups in Organic Synthesis" (hereinafter referred to merely as the "literature"), Chap. 7 (pp. 218~287). Examples of protective groups for the amino of phenylglycylamido group and p-hydroxyphenylglycylamido group are those disclosed in the literature, Chap. 7 (pp. 218~287). Examples of protective groups for the hydroxyl of p-hydroxyphenylglycylamido group are those disclosed in the literature, Chap.2 (pp. 10~72).

Exemplary of the lower alkoxyl represented by $R^2$ are straight-chain or branched $C_{1-4}$ alkoxyl groups such as methoxy, ethoxy, n-propoxy, isopropoxy, n-butoxy, isobutoxy, sec-butoxy and tert-butoxy groups.

Exemplary of the lower acyl represented by $R^2$ are straight-chain or branched $C_{1-4}$ acyl groups such as formyl, acetyl, propionyl, butyryl and isobutyryl.

Examples of protective groups for the protected hydroxyl in the lower alkyl represented by $R^2$ and substituted with hydroxyl or protected hydroxyl, and for the protected hydroxyl represented by R are those disclosed in the literature, Chap. 2 (pp. 10~72). The substituted lower alkyl represented by $R^2$ may have as its substituent(s) one or at least two same or different groups selected from among hydroxyl and the protected hydroxyl groups. Such substituent(s) may be positioned on at least one carbon atom of the alkyl.

Exemplary of the carboxylic acid protecting group represented by $R^3$ are allyl, benzyl, p-methoxybenzyl, p-nitrobenzyl, diphenylmethyl, trichloromethyl, trichloroethyl, tert-butyl, and those disclosed in the literature, Chap. 5 (pp. 152~192).

Examples of substituents for the 1-alkenyl which is represented by $R^4$ and $R^5$ and which may have a substituent can be a halogen atom, hydroxyl, nitro, cyano, aryl, lower alkyl, amino, mono lower alkylamino, di lower alkylamino, mercapto, alkylthio or arylthio represented by the group $R^6S—$ (wherein $R^6$ is lower alkyl or aryl), formyloxy, acyloxy represented by the group $R^6COO—$ (wherein $R^6$ is as defined above), formyl, acyl represented by the group $R^6CO—$ (wherein $R^6$ is as defined above), alkoxyl or aryloxy represented by the group $R^6O—$ (wherein $R^6$ is as defined above), carboxyl, alkoxycarbonyl or aryloxycarbonyl represented by the group $R^6OCO—$ (wherein $R^6$ is as defined above), etc. The 1-alkenyl represented by $R^4$ and $R^5$ may have on the same carbon atom or different carbon atoms one or more substituents which are selected from among the above substituents and which may be the same or different.

Examples of lower alkylsulfonyloxy or substituted lower alkylsulfonyloxy represented by X are methanesulfonyloxy, trifluoromethanesulfonyloxy and trichloromethanesulfonyloxy. Examples of arylsulfonyloxy or substituted arylsulfonyloxy are benzenesulfonyloxy and toluenesulfonyloxy.

The 3-cephem compound of the formula (1) and to be used as the starting material is prepared, for example, by one of the following processes disclosed in literature, depending on the kind of X.

When X is a halogen atom, the compound can be prepared by reacting a reactive chloro compound (such as phosphorus trichloride or phosphorus oxychloride) with a 3-hydroxycephem compound (I) serving as the starting material in dimethylformamide (see JP-A-116095/1974)

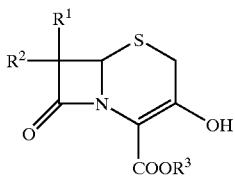

(I)

wherein R¹, R² and R³ are as defined above.

When X is lower alkylsulfonyloxy which may have a substituent or arylsulfonyloxy which may have a substituent, the compound can be prepared by reacting a 3-hydroxycephem compound of the formula (I) with a lower alkylsulfonic anhydride which may have a substituent or an arylsulfonic anhydride which may have a substituent [Journal of Organic Chemistry, 54, 4962 (1989)].

According to the present invention, an alkenyl halide of the formula (2), a nickel catalyst, a metal up to −0.3 (V/SCE) in standard oxidation reduction potential and a compound of a metal having a higher standard oxidation reduction potential than the metal are caused to act on the 3-cephem compound of the formula (1) and prepared by the above process, in an organic solvent, whereby a 3-alkenylcephem compound of the formula (3) [the formula (3a) given below] can be prepared with ease.

Alternatively, a 3-norcephem compound [of the formula (3b) given below] can be obtained by replacing the solvent with a water-containing organic solvent under the same condition

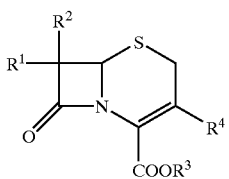

(3a)

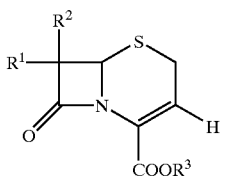

(3b)

wherein R¹, R², R³ and R⁴ are as defined above.

When the solvent used is a water-containing solvent, the 3-norcephem compound of the formula (3b) is obtained presumably because addition of a hydrogen ion occurs before the anion at the 3-position of the compound (1) resulting from reduction undergoes a coupling reaction with the compound (2).

Examples of 1-alkenyl halide compounds of the formula (2) for use in the present invention are vinyl iodide, vinyl chloride, vinyl bromide, 1-cis-propenyl bromide, 1-butenyl bromide, 2-methyl-1-propenyl bromide, 1-methyl-1-propenyl bromide, 1,2-dimethyl-1-propenyl bromide, 3-phenyl-1-propenyl bromide, etc. The compound of the formula (2) is used usually in an amount of 1 to 10 moles, preferably 1 to 4 moles, per mole of the compound of the formula (1).

Examples of nickel catalysts usable are nickel fluoride, nickel chloride, nickel bromide, nickel iodide, nickel nitrate, nickel sulfate, nickel perchlorate, nickel acetate and like nickel salts of fatty acids, tetraethylammoniumnickel(II) tetrachloride, tetraethylammoniumnickel (II) tetrabromide, hexamminenickel (II) chloride, hexamminenickel(II) bromide, dinitrotetramminenickel(II), tris(ethylenediamine) nickel(II) chloride, tris(ethylenediamine)nickel(II) sulfate, dinitrobis(ethylenediamine)nickel(II), bis(N,N-dimethylethylenediamine)nickel(II) perchlorate, dichloro (bipyridyl)nickel(II), dibromo(bipyridyl)nickel(II), chloro (cyclopentadienyl)(triphenylphosphine)nickel(II), dichloro (triphenylphosphine)nickel(II), dibromo (triphenylphosphine)nickel(II) and like nickel(II) complexes, tetrakis(triphenylphosphine)nickel(0), tris (triphenylphosphine)nickel(0), nickel(0) acetylacetonate, nickel(0) hexafluoroacetylacetonate and like nickel(0) complexes. These metallic compounds may be used singly, or at least two of them are usable in mixture.

It is desirable to use the catalyst usually in an amount of 0.01 to 10 moles, preferably 0.1 to 1 mole, per mole of the compound of the formula (1).

Examples of metals having a standard oxidation-reduction potential of up to −0.3 (V/SCE) are magnesium, aluminum, manganese, zinc, iron, tin, lead, etc., among which aluminum is desirable to use. The shape of these metals is not limited particularly but can be any of a wide variety of forms such as powder, plate, foil, lump and wire. Preferably, the metal to be used is in the form of a powder or foil. The particle size of the powdery metal is preferably about 10 to about 300 mesh although variable over a wide range. These metals are used usually in an amount of about 1 to about 50 moles, preferably about 1 to about 10 moles, per mole of the compound of the formula (1).

In case the metal is used less than one mole per mole of the compound of the formula (1), unreacted compound (1) remains which is undesirable to cause decrease in yield and purity of the desired compound.

Examples of metal compounds having a higher standard oxidation-reduction potential than the above metals are lead compounds (such as lead fluoride, lead chloride, lead bromide, lead iodide, lead nitrate, lead sulfate, lead perchlorate, lead borate, lead carbonate, lead phosphate and like inorganic salts of lead, lead acetate, lead oxalate, lead stearate and like fatty acid salts of lead, lead oxide and lead hydroxide), copper compounds (such as copper fluoride, copper chloride, copper bromide, copper iodide, copper nitrate, copper sulfate, copper perchlorate, copper carbonate and like inorganic salts of copper, copper acetate, copper oxalate and like fatty acid salts of copper, copper oxide and copper hydroxide), titanium compounds (such as titanium fluoride, titanium chloride, titanium bromide, titanium iodide, titanium nitrate and titanium sulfate), bismuth compounds (such as bismuth fluoride, bismuth chloride, bismuth bromide, bismuth iodide, bismuth nitrate, bismuth sulfate and bismuth oxide), antimony compounds (such as antimony fluoride, antimony chloride, antimony bromide and antimony iodide). Among these metals, preferable is lead compound.

These metal compounds are used usually in an amount of 0.001 to 10 moles, preferably 0.01 to 3 moles, per mole of the compound of the formula (1).

When at least two of these metallic compounds are used in combination, it is accordingly desirable to use each of at least two metallic compounds in the amount mentioned above.

Examples of combinations each comprising a metal up to −0.3 (V/SCE) in standard oxidation reduction potential and a compound of a metal having a higher standard oxidation reduction potential than the metal are aluminum/lead compound, aluminum/bismuth compound, manganese/ aluminum compound, manganese/lead compound, zinc/lead compound, magnesium/bismuth compound, magnesium/bismuth compound, magnesium/copper compound, tin/titanium compound, tin/bismuth compound, etc. The combination of aluminum/lead compound permits reduction to proceed smoothly and is therefore preferred.

Examples of useful solvents are dimethylacetamide (DMA), dimethylformamide, 1-methyl-2-pyrrolidinone (NMP), hexamethylphosphoric triamide and like amides, acetonitrile, propionitrile, butyronitrile, isobutyronitrile, valeronitrile and like nitriles, dimethylimidazole (DMI), dimethyl sulfoxide, tetrahydrofuran (THF), dioxane, etc. These solvents may be used singly, or at least two of them may be used in mixture.

These solvents, each serviceable as the main solvent, can be used as mixed with other usual solvents, such as methyl formate, ethyl formate, propyl formate, butyl formate, methyl acetate, ethyl acetate, propyl acetate, butyl acetate, methyl propionate, ethyl propionate and like lower alkyl esters of lower alkylcarboxylic acids, diethyl ether, ethyl propyl ether, ethyl butyl ether, dipropyl ether, diisopropyl ether, dibutyl ether, methyl cellosolve, dimethoxyethane and like ethers, tetrahydrofuran, dioxane and like cyclic ethers, benzene, toluene, xylene, chlorobenzene, anisole and like substituted or unsubstituted aromatic hydrocarbons, pentane, hexane, heptane, octane and like hydrocarbons, cyclopentane, cyclohexane, cycloheptane, cyclooctane and like cycloalkanes, dichloromethane, chloroform, dichloroethane, trichloroethane, dibromoethane, propylene dichloride, carbon tetrachloride, Freons and like halogenated hydrocarbons.

Especially preferable are solvent mixtures consisting primarily of diemthylformamide, 1-methyl-2-pyrrolidinone or dimethyl sulfoxide.

The water-containing organic solvents for use in preparing 3-norcephem compounds usually contains 0.2 to 75%, preferably 1 to 40%, of water.

It is desirable to use such solvents in an amount of about 0.5 to about 206 liters, preferably about 1 to about 50 liters, per kilogram of the compound of the formula (1).

The reaction is conducted usually at −10 to 80° C., preferably 0 to 50° C. The reaction of the invention proceeds favorable even at a temperature around room temperature.

The compound of the formula (3) to be obtained by the present invention can be prepared substantially as a pure product by treating the reaction mixture through a usual extraction procedure or crystallization procedure after the completion of reaction. The product can of course be purified alternatively by other method.

In the case where the compound prepared by the present invention is of the formula (3) wherein $R^1$ is protected amino, and $R^2$ is a hydrogen atom [compound (3-1)], this compound is subjected to an amino deprotecting reaction disclosed, for example, in Recent Advances in the Chemistry of β-Lactam Antibiotics, 109 (1980), whereby a 7-amino-3-cephem compound (3-2) can be derived. It is of course possible to derive the 7-amino-3-cephem compound (3-2) directly from a compound of the formula (1) wherein $R^1$ is amino, and $R^2$ is a hydrogen atom by the process of the invention

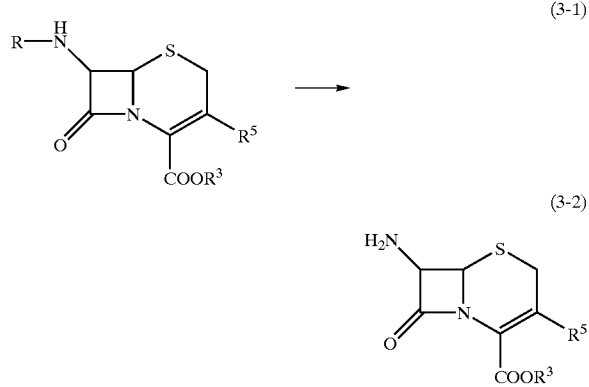

wherein $R^3$ and $R^5$ are as defined above, and R is a protective group for the amino.

The 7-amino-3-cephem compound (3-2) obtained is used as an important intermediate for preparing useful antimicrobial drugs having a wide antibacterial spectrum.

For example, a compound (3-2) wherein $R^5$ is vinyl can be made into the oral antibiotic cefixime by the process disclosed in JP-B-20435/1988, or the compound (3-2) can be made into cefdinir (Katsuharu Sakai, "Handbook of Recent Antibiotics," 9th ed., p. 86, 1994).

Furthermore, the oral antibiotic ceftibuten can be derived from a compound (3-2) wherein $R^5$ is a hydrogen atom by the process disclosed in Pure & Appl. Chem., 59, 1041 (1987).

According to the invention, the substituents of $R^1$, $R^2$ and $R^3$ in the compound of the formula (1) do not participate in the reaction, permitting the reaction to proceed regardless of the kind thereof and affording a compound of the formula (3) which can be used as an intermediate for preparing useful nonnatural antimicrobial drugs.

BEST MODE OF CARRYING OUT THE INVENTION

The present invention will be described below in detail with reference to examples and reference examples, whereas the invention is in no way limited to these examples.

EXAMPLE 1

A 200 mg quantity of a compound of the formula (1) wherein $R^1$=phenylacetamido, $R^2$=H, $R^3$=diphenylmethyl, X=—$OSO_2CF_3$ (1a), 11 mg of lead bromide, 35 mg of dibromo(bipyridyl)nickel complex and 65 mg of aluminum were weighed out, 4 ml of dimethylformamide (DMF) and 180 mg of vinyl bromide were added to these compounds, and the resulting mixture was stirred at 22° C. to 25° C. for 1 hour. The reaction mixture was subjected to extraction with ethyl acetate and 5% hydrochloric acid, and an organic layer obtained was dried over magnesium sulfate and thereafter purified by column chromatography (ethyl acetate/toluene=1/5), affording 145 mg of a compound of the formula (3a) wherein $R^1$=phenylacetamido, $R^2$=H, $R^3$=diphenylmethyl, $R^4$=vinyl (3a-1). 91% in yield.

1H NMR (300 MHz, DMSO-$d_6$) δ 3.49 (d, J=14 Hz, 1H), 3.57 (d, J=14 Hz, 1H), 3.58 (d, J=18 Hz, 1H), 3.91 (d, J=18 Hz, 1H), 5.18 (d, J=5.1 Hz, 1H), 5.28 (d, J=11 Hz, 1H), 5.63 (d, J=17 Hz, 1H), 5.75 (dd, J=5.1, 8.1 Hz, 1H), 6.70 (dd, J=11, 17 Hz, 1H), 6.939 (s, 1H), 9.17 (d, J=8.1 Hz, 1H), 7.19~7.46 (m, 15H).

EXAMPLE 2

A 200 mg quantity of a compound of the formula (1) wherein $R^1$=phenylacetamido, $R^2$=H, $R^3$=p-methoxybenzyl, X=—OSO$_2$CF$_3$ (1b), 12 mg of lead bromido, 38 mg of dibromo(bipyridyl)nickel complex and 70 mg of aluminum were weighed out, 4 ml of DMF and 190 mg of vinyl bromide were added to these compounds, and the resulting mixture was treated in the same manner as in Example 1, affording 153 mg of a compound of the formula (3a) wherein R$^1$=phenylacetamido, R$^2$=H, R$^3$=p-methoxybenzyl, R$^4$=vinyl (3a-2). 89% in yield.

1H NMR (300 MHz, CDCl$_3$) δ 3.44 (d, J=18 Hz, 1H), 3.60 (d, J=16 Hz, 1H), 3.61 (d, J=18 Hz, H), 3.67 (d, J=16 Hz, 1H), 3.79 (s, 3H), 4.92 (d, J=4.4 Hz, 1H), 5.16 (d, J=14 Hz, 1H), 5.21 (d, J=14 Hz, 1H), 5.31 (d, J=11 Hz, 1H), 5.43 (d, J=17 Hz, 1H), 5.81 (dd, J=4.4, 9 Hz, 1H), 6.26 (d, J=9 Hz, 1H), 7.08 (dd, J=44, 17 Hz, 1H), 6.85~7.40 (m, 9H).

EXAMPLE 3

A 200 mg quantity of a compound of the formula (1) wherein R$^1$=phenylacetamido, R$^2$=H, R$^3$=diphenylmethyl, X=—OSO$_2$CH$_3$ (1c), 12 mg of lead bromide, 38 mg of dibromo(bipyridyl)nickel complex and 71 mg of aluminum were weighed out, 4 ml of DMF and 190 mg of vinyl bromide were added to these compounds, and the resulting mixture was treated in the same manner as in Example 1, affording 157 mg of a compound of the formula (3a-1). 90% in yield.

1H NMR spectrum of the compound obtained was identical with that of the compound obtained in Example 1.

EXAMPLE 4

A 200 mg quantity of a compound of the formula (1) wherein R$^1$=phenylacetamido, R$^2$=H, R$^3$=p-methoxybenzyl, X=—OSO$_2$CH$_3$ (1d), 13 mg of lead bromide, 42 mg of dibromo(bipyridyl)nickel complex and 77 mg of aluminum were weighed out, 4 ml of DMF and 200 mg of vinyl bromide were added to these compounds, and the resulting mixture was treated in the same manner as in Example 1, affording 165 mg of a compound of the formula (3a-2). 87% in yield.

1H NMR spectrum of the compound obtained was identical with that of the compound obtained in Example 2.

EXAMPLE 5

A 200 mg quantity of a compound of the formula (1) wherein R$^1$=phenylacetamido, R$^2$=H, R$^3$=diphenylmethyl, X=—OSO$_2$C$_6$H$_4$—CH$_3$-p (1e), 11 mg of lead bromide, 34 mg of dibromo(bipyridyl)nickel complex and 63 mg of aluminum were weighed out, 4 ml of DMF and 180 mg of vinyl bromide were added to these compounds, and the resulting mixture was treated in the same manner as in Example 1, affording 136 mg of a compound of the formula (3a-1). 88% in yield.

1H NMR spectrum of the compound obtained was identical with that of the compound obtained in Example 1.

EXAMPLE 6

A 200 mg quantity of a compound of the formula (1) wherein R$^1$=phenylacetamido, R$^2$=H, R$^3$=p-methoxybenzyl, X=—OSO$_2$C$_6$H$_4$—CH$_3$-p (1f), 11 mg of lead bromide, 36 mg of dibromo(bipyridyl)nickel complex and 67 mg of aluminum were weighed out, 4 ml of DMF and 190 mg of vinyl bromide were added to these compounds, and the resulting mixture was treated in the same manner as in Example 1, affording 149 mg of a compound of the formula (3a-2). 90% in yield.

1H NMR spectrum of the compound obtained was identical with that of the compound obtained in Example 2.

EXAMPLE 7

A 200 mg quantity of a compound of the formula (1) wherein R$^1$=phenylacetamido, R$^2$=H, R$^3$=diphenylmethyl, X=Cl (1g), 13 mg of lead bromide, 43 mg of dibromo (bipyridyl)nickel complex and 79 mg of aluminum were weighed out, 4 ml of DMF and 220 mg of vinyl bromide were added to these compounds, and the resulting mixture was treated in the same manner as in Example 1, affording 167 mg of a compound of the formula (3a-1). 86% in yield.

1H NMR spectrum of the compound obtained was identical with that of the compound obtained in Example 1.

EXAMPLE 8

A 200 mg quantity of a compound of the formula (1) wherein R$^1$=phenylacetamido, R$^2$=H, R$^3$=p-methoxybenzyl, X=Cl (1h), 15 mg of lead bromide, 47 mg of dibromo (bipyridyl)nickel complex and 87 mg of aluminum were weighed out, 4 ml of DMF and 240 mg of vinyl bromide were added to these compounds, and the resulting mixture was treated in the same manner as in Example 1, affording 175 mg of a compound of the formula (3a-2). 82% in yield.

1H NMR spectrum of the compound obtained was identical with that of the compound obtained in Example 2.

EXAMPLE 9

A 200 mg quantity of a compound (1b), 14 mg of lead bromide, 43 mg of dibromo(bipyridyl)nickel complex and 80 mg of aluminum were weighed out, 4 ml of DMF and 230 mg of 1-cis-propenyl bromide were added to these compounds, and the resulting mixture was treated in the same manner as in Example 1, affording 167 mg of a compound of the formula (3a) wherein R$^1$=phenylacetamido, R$^2$=H, R$^3$=p-methoxybenzyl, R$^4$=cis-1-propenyl (3a-3). 85% in yield.

1H NMR (300 MHz, CDCl$_3$) δ 1.53 (dd, J=1.7, 7.1 Hz, 3H), 3.24 (d, J=17.8 Hz, 1H), 3.45 (d, J=17.8 Hz, 1H), 3.60 (d, J=15.6 Hz, 1H), 3.69 (d, J=15.6 Hz, 1H), 3.80 (s, 3H), 4.97 (d, J=4.8 Hz, 1H), 5.14 (s, 2H), 5.64 (dq, J=7.1, 11.5 Hz, 1H), 5.79 (dd, J=4.8, 9.1 Hz, 1H), 6.07 (dd, J=1.7, 11.5 Hz, 1H), 6.13 (d, J=9.1 Hz, 1H), 6.82~6.92, 7.20~7.43 (m, 9H).

EXAMPLE 10

The same reaction as in Example 1 was conducted with the exception of adding 200 mg of water to the reaction system, consequently affording 144 mg of a compound of the formula (3b) wherein R=phenylacetamido, R$^2$=H, R$^3$=diphenylmethyl (3b-1). 94% in yield.

1H NMR (300 MHz, CDCl$_3$) δ 3.46 (dd, J=6.2, 19.0 Hz, 1H), 3.67 (dd, J=2.2, 19.0 Hz, 1H), 3.71, 3.79 (ABq, J=15.8 Hz, 2H), 5.04 (d, J=4.3 Hz, 1H), 6.00 (dd, J=4.3, 9.0 Hz, 1H), 6.19 (d, J=9.0 Hz, 1H), 6.71 (dd, J=2.2, 6.2 Hz, 1H), 7.03 (s, 1H), 7.35~7.58 (m, 15H).

EXAMPLE 11

The same reaction as in Example 2 was conducted with the exception of adding 200 mg of water to the reaction system, consequently affording 138 mg of a compound of the formula (3b) wherein R$^1$=phenylacetamido, R$^2$=H, R$^3$=p-methoxybenzyl (3b-2). 92% in yield.

1H NMR (300 MHz, CDCl$_3$) δ 3.33 (dd, J=6.3, 19.2 Hz, 1H), 3.53 (dd, J=2.7, 19.2 Hz, 1H), 3.59, 3.71 (ABq, J=16.1 Hz, 2H), 3.80 (s, 3H), 4.90 (d, J=5.1 Hz, 1H), 5.15, 5.22 (ABq, J=11.8 Hz, 2H), 5.86 (dd, J=5.1, 9.2 Hz, 1H), 6.15 (d, J=9.2 Hz, 1H), 6.50 (dd, J=2.7, 6.3 Hz, 1H), 6.86~7.35 (m, 9H).

EXAMPLES 12 TO 16

Compounds (3a-1) were obtained by repeating the same reaction as in Example 1 and replacing the reaction solvent with the following solvents. Table 1 shows the results.

TABLE 1

| Ex. | solvent | yield (%) |
| --- | --- | --- |
| 12 | NMP | 87 |
| 13 | DMA | 85 |
| 14 | DMI | 85 |
| 15 | THF | 82 |
| 16 | dioxane | 80 |

1H NMR spectrum of the compound (3a-1) obtained in each example was identical with that of the compound obtained in Example 1.

EXAMPLES 17 TO 21

Compounds (3a-1) were obtained by repeating the same reaction as in Example 1 and replacing the lead bromide with the following metallic salts. Table 2 shows the results.

TABLE 2

| Ex. | metallic salt | yield (%) |
| --- | --- | --- |
| 17 | bismuth (III) chloride | 84 |
| 18 | titanium (IV) chloride | 82 |
| 19 | lead (II) chloride | 80 |
| 20 | antimony (III) chloride | 76 |
| 21 | copper (II) chloride | 71 |

1H NMR spectrum of the compound (3a-1) obtained in each example was identical with that of the compound obtained in Example 1.

EXAMPLES 22 TO 25

Compounds (3a-1) were obtained by repeating the same reaction as in Example 1 and replacing the aluminum with the following metals. Table 3 shows the results.

TABLE 3

| Ex. | metal | yield (%) |
| --- | --- | --- |
| 22 | zinc | 89 |
| 23 | tin | 85 |
| 24 | magnesium | 79 |
| 25 | manganese | 72 |

1H NMR spectrum of the compound (3a-1) obtained in each example was identical with that of the compound obtained in Example 1.

REFERENCE EXAMPLE 1

Through the following procedure, cefixime can be derived from the 3-vinylcephem compound (3a-1 or 3a-2) obtained in Example 1 or 2.

The compound (3a-1) or (3a-2) is reacted with phosphorus pentachloride/pyridine reagent in methylene chloride solvent, and the reaction mixture is thereafter cooled to −35° C. and treated with methanol to produce 7-amino-3-vinylcephem hydrochloride (4). Phenol is added to the compound (4), followed by reaction at 45° C. for 1 hour to obtain 7-amino-3-vinylcephem-4-carboxylic acid (5). Cefixime can be derived from the compound (5) by the reaction of the 7-position side chain and final deprotection reaction through the process disclosed in JP-B-20435/1988.

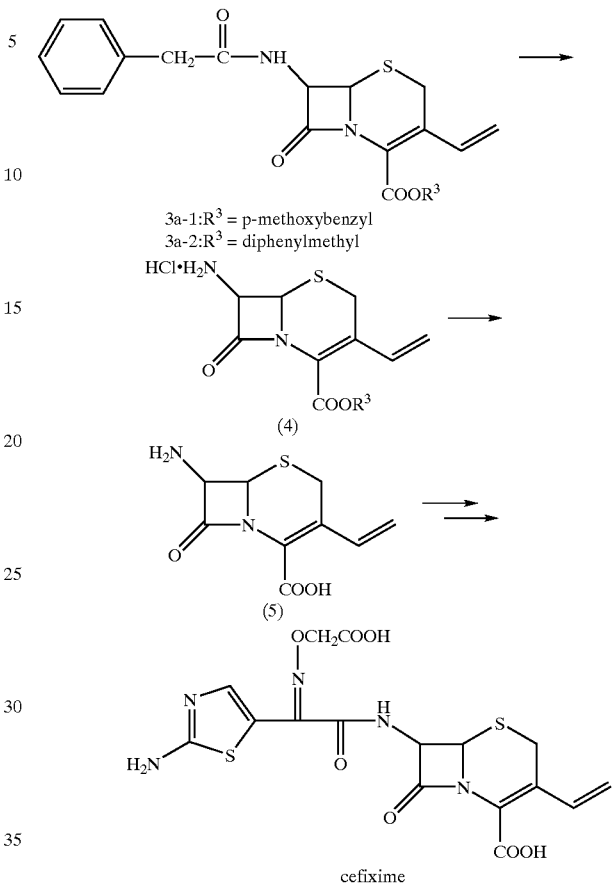

REFERENCE EXAMPLE 2

The 3-norcephem compound (3b-1) obtained in Example 10 is treated in the same manner as in Reference Example 1 to obtain 7-amino-3-norcephem hydrochloride (6). Ceftibuten can be derived from this compound through the process disclosed in Pure & Appl. Chem., 59, 1041 (1987).

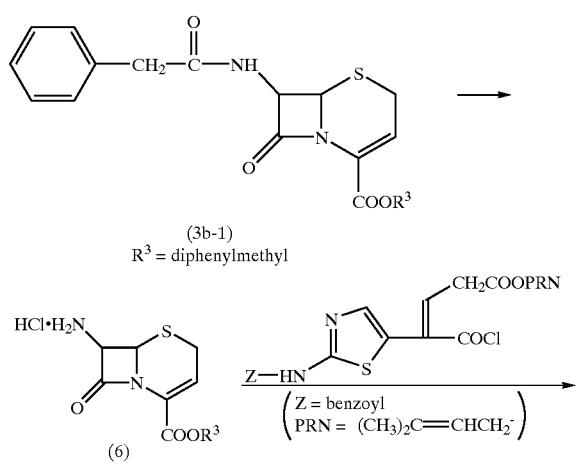

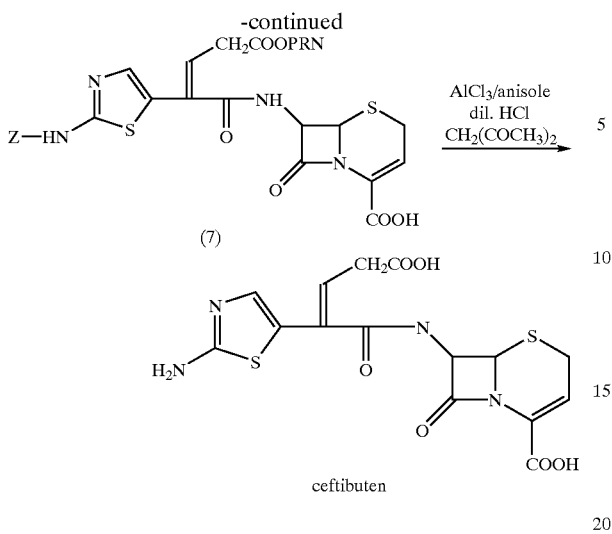

(7)

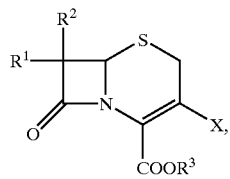

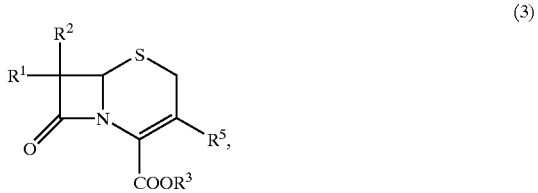

ceftibuten

INDUSTRIAL APPLICABILITY

The present invention provides a process for preparing a 3-alkenylcephem compound or 3-norcephem compound which is an intermediate for preparing useful nonnatural antimicrobial drugs having a wide antibacterial spectrum.

What is claimed is:

1. A process for preparing a compound of the formula (3):

(3)

wherein $R^1$ is a hydrogen atom, halogen atom, amino or protected amino, $R^2$ is a hydrogen atom, halogen atom, lower alkoxyl, lower acyl, hydroxyl, protected hydroxyl, or lower alkyl, optionally having a hydroxyl or protected hydroxyl as a substituent, $R^3$ is a hydrogen atom or carboxylic acid protective group, and $R^5$ is a hydrogen atom or 1-alkenyl optionally having a substituent selected from the group consisting of a halogen atom, hydroxyl, nitro, cyano, aryl, lower alkyl, amino, mono lower alkylamino, di lower alkylamino, mercapto, alkylthio or arylthio having the formula $R^6S-$, wherein $R^6$ is lower alkyl or aryl, formyloxy, acyloxy having the formula $R^6COO-$, wherein $R^6$ is the same as defined above, formyl, acyl having the formula $R^6CO-$, wherein $R^6$ is the same as defined above, alkoxyl or aryloxy having the formula $R^6O-$, wherein $R^6$ is the same as defined above, carboxyl, and alkoxycarbonyl or aryloxycarbonyl having the formula $R^6OCO-$, wherein $R^6$ is the same as defined above, which comprises reacting in a solvent a compound of formula (1):

(1)

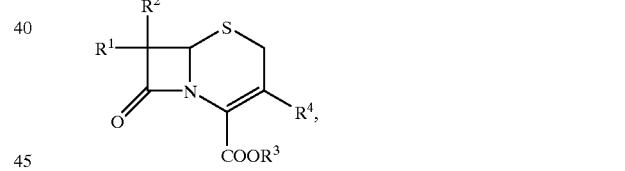

wherein $R^1$, $R^2$ and $R^3$ are the same as defined above, and X is a halogen atom, lower alkylsulfonyloxy optionally having a substituent selected from the group consisting of a halogen atom and an alkyl having 1 to 4 carbon atoms, or an arylsulfonyloxy optionally having a substituent selected from the group consisting of a halogen atom and an alkyl group having 1 to 4 carbon atoms, with a nickel catalyst, a metal up to −0.3 (V/SCE) in standard oxidation reduction potential, a compound of a metal having a higher standard oxidation reduction potential than the metal, and a compound having the formula (2):

$$R^4 - Y$$

wherein $R^4$ is 1-alkenyl optionally having a substituent selected from the same substituents as defined above for $R^5$, and Y is a halogen atom, to obtain the compound of formula (3).

2. The process according to claim 1, wherein at least one mole of the metal up to −0.3 (V/SCE) in standard oxidation reduction potential, and 0.001 to 10 moles of the compound of the metal having a higher standard oxidation reduction potential than the metal, are used per mole of the compound of formula (1).

3. The process according to claim 1, wherein the solvent is an organic solvent, and wherein the process produces a compound of the formula (3a):

(3a)

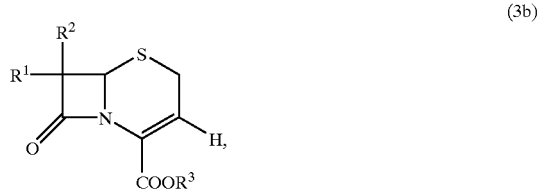

wherein $R^1$, $R^2$, $R^3$ and $R^4$ are the same as defined in claim 1.

4. The process according to claim 1, wherein the solvent is a water-containing organic solvent, and wherein the process produces a compound of the formula (3b):

(3b)

wherein $R^1$, $R^2$ and $R^3$ are the same as defined in claim 1.

* * * * *